United States Patent [19]

Bauman

[11] Patent Number: 4,557,256
[45] Date of Patent: Dec. 10, 1985

[54] EXAMINATION DEVICE WITH AN IMPROVED BLADE CONNECTION

[76] Inventor: Jack Bauman, 1677 San Onofre Drive, Pacific Palisades, Calif. 90272

[21] Appl. No.: 633,633

[22] Filed: Jul. 23, 1984

[51] Int. Cl.⁴ .............................................. A61B 1/06
[52] U.S. Cl. .................................................... 128/11
[58] Field of Search ..................... 128/10, 11, 15, 16, 128/17, 18, 6

[56] References Cited

U.S. PATENT DOCUMENTS

| | | | |
|---|---|---|---|
| 2,289,226 | 7/1942 | Von Foregger | 128/16 |
| 2,433,705 | 12/1947 | Palmeter | 128/10 |
| 2,649,087 | 8/1953 | Allyn et al. | 128/6 |
| 3,426,749 | 2/1969 | Jephcott | 128/11 |
| 3,598,113 | 8/1971 | Moore | 128/11 |
| 3,766,909 | 10/1973 | Ozbey | 128/11 |
| 3,771,514 | 11/1973 | Huffman et al. | 128/11 |
| 3,826,248 | 7/1974 | Gobels | 128/11 |
| 4,037,588 | 7/1977 | Heckele | 128/11 |
| 4,114,609 | 9/1977 | Moses | 128/11 |
| 4,273,112 | 6/1981 | Heine et al. | 128/11 |
| 4,295,465 | 10/1981 | Racz et al. | 128/11 |
| 4,306,547 | 12/1981 | Lowell | 128/4 |
| 4,320,745 | 3/1982 | Bhitiyakul et al. | 128/11 |

Primary Examiner—William H. Grieb
Attorney, Agent, or Firm—Fulwider, Patton, Rieber, Lee & Utecht

[57] ABSTRACT

This invention relates to an improved means to detachably secure a blade to a handle of medical examining devices such as laryngoscopes, which will secure the blade to the handle in at least two positions in an L-shaped configuration, one position being an operating position and one position being a ready position.

7 Claims, 5 Drawing Figures

EXAMINATION DEVICE WITH AN IMPROVED BLADE CONNECTION

BACKGROUND OF THE INVENTION

This invention generally relates to examining devices such as laryngoscopes and particularly to an improved system to connect the blade to the handle of a laryngoscope.

Laryngoscopes generally comprise a blade and a cooperating handle which are connected together in a generally L-shaped configuration. The handle normally serves as an enclosure for one or more batteries which energize a light bulb secured adjacent to the blade and connected by wires or other electrical conducting means to the batteries in the handle. The switch for activating the light bulb is usually positioned immediately adjacent to the light bulb and is operated by the blade when it is connected to on the handle. The light from the bulb passes through a clear light conductor to the distal end of the blade to illuminate the patient's mouth and larynx during the examination thereof by medical personnel. The surface on the blade adjacent to the handle is used to press against the tongue and mandible of a patient in a supine position in order to prevent the patient's tongue from obstructing the visual examination of the larynx by medical personnel.

While the instrument is useful for examining the larynx, the primary function of the laryngoscope is to expose the larynx in order to facilitate the insertion of an endotracheal tube. The surface of the laryngoscope blade adjacent the handle is urged against the tongue and mandible to expose the larynx in such procedures and the opposite blade surface is positioned opposing the upper front teeth of the patient.

When using the laryngoscope there is a tendency to use the upper front teeth of the patient as a fulcrum for the blade in exposing the larynx and in order to minimize damage to the patient's front teeth that portion of the blade which comes in contact with the patient's front teeth is is made to yield when pressed against the patient's teeth to avoid chipping or breaking the teeth.

In many of the laryngoscopes in use today, the switch which turns on the light bulb is actuated when the blade is connected to the handle. To turn the light off the blade must be disengaged from the handle. However, it is frequently desirable to connect the blade to the handle without actuating the lighting means and moreover it is frequently desirable to turn the light off without disengaging the blade from the handle.

In many of the prior art laryngoscopes, the means for connecting the blade to the handle generally comprises a depending appendage at the proximal end of the blade generally in the shape of a boot. The appendage fits into an open channel on the top of the handle and the front end of the boot-shaped appendage hooks under a pivot rod at the front end of the channel. Ball detents are provided in the depending section of the blade which snap into position in the dimples provided in the walls of the channel to thereby fix the position of the blade with respect to the handle. If the ball detents become disengaged from the dimples, then the blade is readily disconnected from the handle. For the medical personnel, usually anesthesiologists, who utilize the laryngoscopes, this frequently poses a problem inasmuch as if the device needs to be used again, both hands must then be available to reconnect the blade to the handle and snap the blade into position to actuate the lighting means.

The present invention provides an improved means to connect the blade to the handle of laryngoscope which resolves many of the aforesaid problems of the prior devices.

SUMMARY OF THE INVENTION

The present invention is directed to an improved system for connecting the blade to the handle of an examining device such as a laryngoscope which provides for a plurality of blade positions within the general L-shaped configuration and particularly to a connecting system which allows for the attachment of the blade to the handle in at least one operating position in which the lighting means is actuated and in at least one ready position in which the lighting means is not activated.

In accordance with the invention, the depending appendage of the blade which interfits with the open channel in the top of the handle is in part shaped like a boot and the front section thereof hooks underneath a pivot rod in the front end of the channel in a conventional fashion. The rear surface of the boot shaped appendage is provided with one or more detents which match the grooves, dimples or other cavities provided in a surface at the rear of the channel. The detents and grooves or dimples provide for at least two blade positions in the L configuration, one a ready position and one an operating position.

Preferably, the rear surface of the channel is adapted to plastically yield a small amount, so that when the detents on the depending appendage of the blade move over the edge of the channel and snap into the groove or dimple provided in the rear channel surface, the front end of the boot-shaped appendage is urged forward against the pivot rod to ensure positive positioning of the blade with respect to the handle.

A light means, usually battery operated, is provided in the handle and a light conductor in the blade which is optically connected to the light source to conduct light from the source to the distal end of the blade to illuminate the field of view when the laryngoscope is in use. The switch for energizing the light is positioned so that it cannot be actuated when the blade is in a ready position but is activated when the blade is put into an operating position.

While the system of the invention is primarily designed for construction of plastic materials in order to reduce the cost thereof, the components can also be formed of metal. In the latter instance the connector means in the handle might be spring loaded or provided with other flexible means to effect the yielding of the surface of the channel which urges the appendage into tighter contact with the pivot rod.

These and other features and advantages of the invention will become more apparent from the following detailed description when taken in conjunction with the accompanying drawings.

BRIEF DESCRIPTION OF THE DRAWINGS

In the drawings, all corresponding parts are numbered the same.

DETAILED DESCRIPTION OF THE INVENTION

Figure 1:
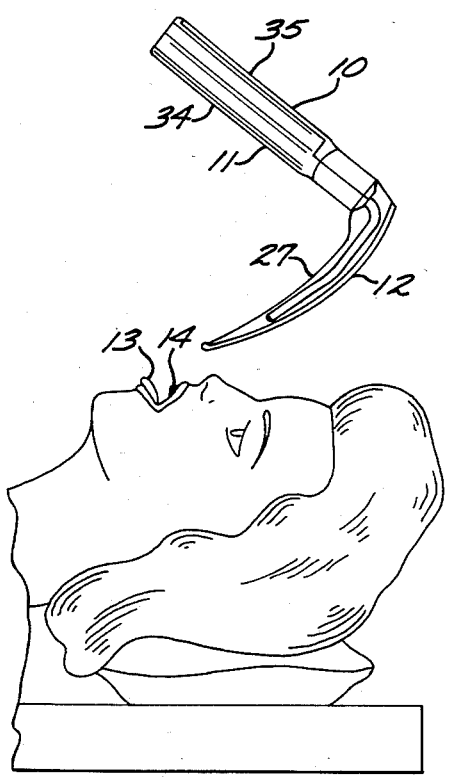
FIG. 1 is a side elevational view of a laryngoscope preparatory to being used on a patient which embodies features of the invention.

Reference is made to the drawings which illustrate a laryngoscope embodying features of the present invention. The instrument is intended for use by medical personnel in the examination of a patient's mouth and larynx and particularly to expose the larynx to facilitate the insertion of an endotracheal tube. As shown in FIG. 1, the laryngoscope 10 which comprises a handle 11 and blade 12 is utilized to depress the patient's tongue and mandible 13. Frequently the patient's front teeth 14 are used as a fulcrum for the blade 12 in order to more completely expose the patient's larynx during the examination of the larynx and the insertion of an endotracheal tube.

Figure 2:
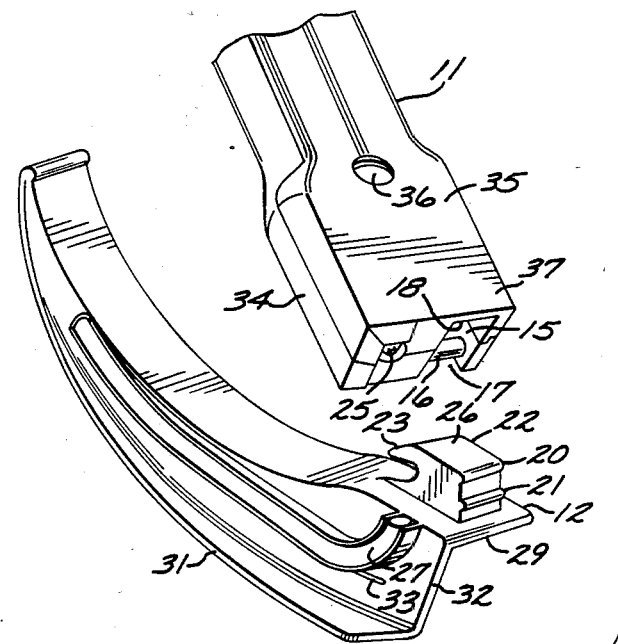
FIG. 2 is a perspective exploded view of the blade and handle of the laryngoscope shown in FIG. 1.

In general as shown in FIG. 2, the laryngoscope 10 comprises a handle 11, a blade 12 and means be detachably secure the blade 12 to the handle 11 into a general L-shaped configuration.

The means used to couple the blade 11 to the handle 12 is best illustrated in FIGS. 2-5. As shown therein, the upper end of the handle 11 has an open channel 15 which is provided with a pivot rod 16 at the front end 17 thereof. A vertical surface 18 at the rear end of the channel 15, has one or more grooves or dimples 19 adapted to seat the detents 20 and 21 on the rear vertical surface 18 of a boot-shaped appendage 22.

The boot shaped appendage 22 interfits into the open channel 15 and is mounted therein in a pivotal fashion. The front end 23 of the boot shaped appendage 22 is hooked under the pivot rod 16 during the pivotal mounting thereof in a conventional fashion. The elongated detents 20 and 21 are formed on the back surface of the boot-shaped appendage 22 which are adapted to interfit into the grooves or dimple 19 in the surface 18 at the rear of the channel 15.

Figure 3:
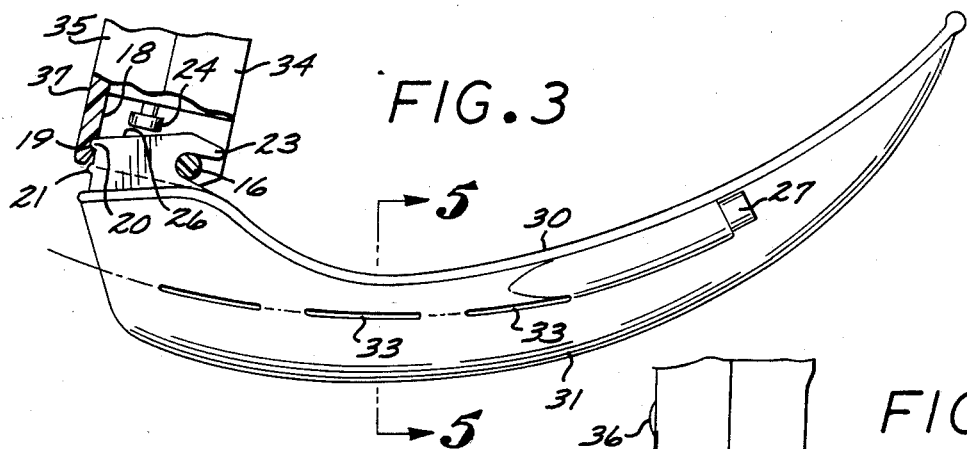
FIG. 3 is a side elevational view partially in section, of the laryngoscope with the blade in a ready position.
Figure 5:
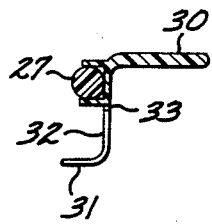
FIG. 5 is a cross sectional view taken along the lines of 5—5 shown in FIG. 3.
Figure 4:
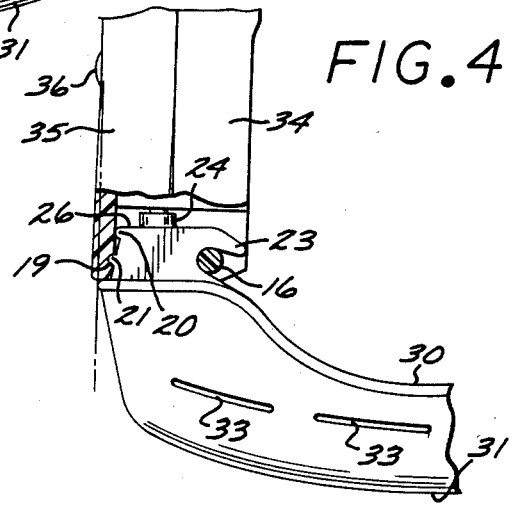
FIG. 4 is a partial side elevational view partially in section, of the laryngoscope with the blade in the operative position.

To mount the blade onto the handle 11, the appendage 22 of the blade 12 is inserted into the open top channel 15 with a pivotal motion so that the front end 23 is hooked under the pivot rod 16. Initially, the elongated first detent 20 moves into engagement with the groove 19 provided in the back wall 18 to thereby urge the appendage 22 into a more firm engagement with the pivot rod 16 and to fix the blade 12 in a ready position as shown in FIG. 3. As shown in FIG. 4, further rotation of the blade 12 causes the displacement of the first detent 20 from the groove 19 and the engagement of the second detent 21 therewith to fix the blade 12 in an operating position. The vertical surface or wall 18 at the rear of the channel 15 is sufficiently yieldable as indicated in FIG. 4 to ensure that appendage 22 firmly engages the pivot rod 16 and thereby locks the positioning of the blade 12 on the handle 11. While the detents 20 and 21 are shown in FIGS. 2-4 as being integral with the appendage 22 and the groove 19 is shown as part of wall 37, it should be clear that it makes little difference if these positions are reversed so long as the detents 20 and 21 and the groove 19 are on opposed faying surfaces.

Preferably, a light switch 24 is provided at the bottom of the channel 15 in a position so that it is activated only when the blade 12 is rotated and locked into an operating position. A light source 25 is provided on the top surface of the handle adjacent to channel 15 and is energized when the light switch 24 is activated. As shown in FIG. 3, when the blade 12 is initially mounted on the handle 11, the first elongated detent 20 engages the groove 19 in the back surface 19 of the cavity 15 to thereby lock the blade 12 in a ready position on the handle 11 but the bottom surface 26 of the appendage 22 does not activate the light switch. In this manner, the blade 12 can be firmly mounted to the handle 11 in a ready position without activating the light switch 22 and thereby turning on the light 23. Further rotation of the blade 12 causes the second detent 21 to engage the groove 19 and to thereby lock the blade 12 in an operating position and simultaneously therewith to activate the light switch 24, which in turn energizes the light source 25.

As best shown in FIGS. 2-4, light is directed from the light source 25 to a position close to the distal end of the blade 12 along the light of sight thereof by means of a light conductor 27 to ensure the proper illumination of a patient's mouth ahnd larynx when the laryngoscope is being used. The proximal end 28 of the conductor 27 is located at the proximal end 29 of the blade 12 so that, when the blade 12 is rotated into its final operating position, the proximal end 28 of the light conductor 27 is immediately adjacent to the light source 25 and there is a realiable and efficient optical coupling therebetween.

The lower portion 30 of the blade 12 which comes in contact with the tongue and mandible 13 of the patient should be rigid, whereas the upper section 31 which comes in contact with the patient's teeth 14 should be yieldable so that, when the blade 12 is urged against the patient's teeth 14 during examination of the larynx, no significant damage thereto occurs. Preferably, the surface 31 which is in contact with the patient's teeth 14 is supported to the rigid portion 30 of the blade 12 by means of a wall or web 32 which is elastically deformable as desribed and claimed in copending application Ser. No. 492,190, filed May 6, 1983. As shown in the drawings, windows or slots 33 are provided in wall 32 to provide the desired flexibility.

A wide variety of blade types and shapes can be employed with the present invention. Additionally, the entire blade can be produced from light conducting plastic materials such as acrylics or polycarbonates in which case there is no need for a separate light conductor element.

The handle 11 which is preferably formed from relatively inexpensive plastic materials generally has an internal cavity which is adapted to hold one or more battery units (not shown) which supply the electrical energy to energize the light source 25. As best shown in FIGS. 2-4, the handle has two separate components 34 and 35 which are urged together by means of a screw 36. The position of this screw connection allows the back wall 37 and thus the surface 18 of the channel 15 to elastically yield when the blade 12 is pivotally mounted onto the handle 11 as shown in FIG. 4. If the handle 11 is manufactured from metal products such as steel, it may be desirable to provide the yieldability of this back wall 27 of the channel 15 by means of a spring loaded connection. Other forms of yieldable construction can also be used to apply pressure to the boot shaped appendage 22 to ensure a positive coupling to the pivot rod 16.

As described incopending application Ser. No. 492,190, filed May 6, 1983, the web or wall 32 connecting the rigid portion 30 of the blade 12 to the surface 31 which comes in contact with the patient's teeth 14 can be made elastically deformable by several means. For example, windows, grooves or pleats either alone or in combination can be employed to provide the necessary flexibility of the upper surface to prevent damage to the patient's teeth 14. Additionally, the web or wall 32 can be made much thinner than the other parts of the blade 12 to provide the required buckling or bending characteristics.

After use, the blade is decoupled from the handle by simply rotating the blade 12 toward the handle 11 and then pushing upwardly on the blade 12 to disengage or unhook the front end 12 of appendage 22 from the pivot rod 16. If the blade is formed of inexpensive plastic material, it may be discarded or, if formed from metal, can be sterilized and reused.

Although the specific embodiment of the invention is described herein in connection with laryngoscopes, it is obvious that the improved means to connect a blade and a handle into an L-shaped configuration can be employed in other examining devices.

Modifications and improvements can be made to the present invention without departing from the inventive concepts thereof.

I claim:

1. In an examining device comprising a blade, a handle, means to detachably secure the blade to the handle in an L-shaped configuration comprising a boot-shaped depending appendage on the proximal end of the blade, the front end of the boot-shaped appendage adapted to hook under a pivot rod in the front end of an open channel provided in the top of the handle and adapted to receive the boot-shaped appendage on the blade, the improvement comprising means to detachably secure the blade to the handle in at least two positions in the L-shaped configuration, one position being an operating position and one position being a ready position.

2. In laryngoscope comprising a blade, a handle, means to detachably secure the blade to the handle in an L-shaped configuration comprising a boot-shaped depending appendage on the proximal end of the blade, the front end of the boot-shaped appendage adapted to hook under a pivot rod in the front end of an open channel provided in the top of the handle and adapted to receive the boot-shaped appendage on the blade, a light source, switching means to energize the light source, and means to conduct the light to the distal end of the blade to illuminate the field of view during the use of the laryngoscope, the improvement comprising means to detachably secure the blade in the handle in at least two positions in the L-shaped configuration, one position being an operating position and one position being a ready position.

3. The laryngoscope of claim 2 wherein the switching means is positioned in the channel so that the switching means is actuated when the blade is in the operating position but is not actuated when in the ready position.

4. The laryngoscope of claims 2 wherein the securing means comprises detents and cooperating cavities on the faying surfaces of the handle and blade.

5. The laryngoscope of claim 4 wherein the faying surface of the handle is elastically yieldable, and urges the appendage into engagement with the pivot rod.

6. The laryngoscope of claim 4 wherein the faying surface of the handle is at the rear of the channel and is provided with at least one cooperating cavity which receives the detents provided on the faying surface of the appendage to thereby engage and hold the blade in the desired position.

7. The laryngoscope of claim 5 wherein the faying surface on the appendage is at the rear or heel of the appendage and is provided with at least two detents.

* * * * *